(12) United States Patent
Mueller et al.

(10) Patent No.: US 6,620,153 B2
(45) Date of Patent: Sep. 16, 2003

(54) INTRAOPERATIVE MYOCARDIAL DEVICE AND STIMULATION PROCEDURE

(76) Inventors: Richard L. Mueller, 2305 Cypress Point, Byron, CA (US) 94514; Douglas Murphy-Chutorian, 151 Lowell Ave., Palo Alto, CA (US) 94301; Stuart D. Harman, 4321 Beechmont Ave., San Jose, CA (US) 95136

( * ) Notice: Subject to any disclaimer, the term of this patent is extended or adjusted under 35 U.S.C. 154(b) by 0 days.

(21) Appl. No.: 09/854,072

(22) Filed: May 11, 2001

(65) Prior Publication Data
US 2003/0073985 A1 Apr. 17, 2003

Related U.S. Application Data

(63) Continuation of application No. 08/664,956, filed on Jun. 13, 1996, now abandoned.

(51) Int. Cl.$^7$ ................................................ A61G 18/20
(52) U.S. Cl. ........................... 606/15; 606/7; 606/10; 606/13

(58) Field of Search ........................ 606/3, 7, 10–17

(56) References Cited

FOREIGN PATENT DOCUMENTS

EP 812574 * 12/1997 .................. 606/7

* cited by examiner

Primary Examiner—David M. Shay
(74) Attorney, Agent, or Firm—Gibson, Dunn & Crutcher LLP

(57) ABSTRACT

An apparatus for stimulating revascularization of myocardium tissue in the ventricular wall of a human heart is disclosed. The apparatus includes means for moving the distal end of an optical fiber element forwardly through the epicardium of the heart and into the myocardium and emitting relatively low power bursts of laser energy from the distal end to form stimulus injury zones that promote capillary growth and tissue revascularization. Each penetration of the optical fiber element may produce multiple stimulus zones spaced radially from or in line with the axis of the optical fiber element. Apparatus for moving the optical fiber element and controlling the laser emissions in a predetermined manner is also disclosed.

13 Claims, 10 Drawing Sheets

INTRAOPERATIVE MYOCARDIAL DEVICE AND STIMULATION PROCEDURE

This application is a continuation of Provisional Serial No. 08/664,956 filed Jun. 13, 1996, now abandoned.

FIELD OF INVENTION

This invention relates to the field of laser surgery, and more particularly to improved laser surgical methods and apparatus for increasing or stimulating revascularization or angiogenesis of myocardial heart tissue and thus the flow of blood to heart muscle.

BACKGROUND OF THE INVENTION

Using various surgical techniques, some of which have been widely taught, medical science has developed several procedures for counteracting the effects of cardiovascular disease including open heart and bypass surgery.

More recently, another alternative form of cardiovascular surgery has been developed which is known as Transmyocardial Revascularization (TMR). Generally, in this TMR procedure, the surgeon accesses the patient's heart by either percutaneous means or by an open incision, then proceeds to utilize a laser apparatus for creating a plurality of channels in the myocardial muscle tissue that forms a wall of a major heart chamber such as the left ventricle. Clinical tests have shown that the creation of a plurality of channels serves to increase flow of blood to the myocardial muscle tissue so as to establish a new vasculature that enables the heart to absorb more oxygen and be revitalized. Various forms of TMR procedures are disclosed in prior art United States patents such as U.S. Pat. No. 4,658,817 (Hardy), U.S. Pat. No. 5,125,926 (Rudko, et al) and U.S. Pat. No. 5,380,316 (Aita, et al) and also, more recently in co-pending application Ser. No. 08/607,782 which is assigned to the assignee of this invention. All of the aforesaid patents and applications disclose a procedure which utilizes laser energy that ablates the myocardial tissue at spaced apart locations to consume it in order to form a plurality of channels in the wall of the ventricular chamber of the patient's heart. As blood flows into each channel formed, a revascularization process takes place which supplies additional oxygen to the heart muscle tissue and thereby revitalizes it. Although the beneficial effects of creating such channels in the wall of the patient's heart chamber have been established, certain risks involved with such procedures have also been recognized. For example, if too many channels are formed during one procedure, there is a risk that a certain patient's heart will react negatively to the trauma of the procedure or become weakened by it in some manner.

The present invention solves the aforesaid problem by providing a method and apparatus that enables the surgeon to stimulate the myocardium to cause revascularization rather than ablate the tissue at several locations to create channels. Thus, for some patients, the stimulation procedure creates a revascularization effect which strengthens the heart's myocardial muscle tissue without negative effects thereto.

It is therefore one object of the invention to provide an improved method and apparatus for causing transmyocardial revascularization by stimulating the myocardium with less laser power, by creating temporary channels with diameters sized so the channels will close with time, and by creating spaced apart stimulation zones within the myocardium.

SUMMARY OF THE INVENTION

The present invention covers a method and apparatus for Transmyocardial Revascularization (TMR) procedures which provides for stimulating the myocardium of the heart muscle rather than creating open channels in it as in prior TMR procedures. Within the context of the present invention, the term "stimulating" or "stimulus" means a TMR procedure wherein channels, zones or pockets of lased tissue are formed in the myocardium which are not open, or do not remain open, to the ventricular chamber of the heart. Revascularization or angiogenesis of the lased channels, zones or pockets occurs by means of introduction of blood born growth and healing factors and stimulated capillary growth surrounding the lased zones or pockets to create an increased supply of oxygen to the tissue and thus a revitalization of the heart muscle.

Revascularization or angiogenesis of the lased channels and/or zones will occur in the following ways: First, blood born growth and healing factors can be introduced to the site of stimulus (injury) as blood follows a lased or mechanical channel created by a laser fiber. The source of new blood and growth factors may be from the ventricle or from the surrounding myocardium. This combination of laser induced injury and blood born healing factors will act together to trigger revascularization. Secondly, the human myocardium displays elements of certain direct blood pathways similar to those found in reptilian hearts. In the present invention these pre-existing pathways can be inter-connected by using stimulus and lasing pockets in the myocardium. The overall effect is to increase the opportunities for capillary beds to become interconnected. Development of collateral coronary vessels is well documented in coronary literature. This can be viewed as an enhanced means for promoting new vessel growth. Lastly, the coronary muscle may be previously injured, thereby creating angina pain for the patient due to the net balance of blood flow and conditions left by a prior heart injury. By stimulating the heart, a new set of injuries (stimulus) is created which triggers a new healing response; in effect, re-injuring the myocardium in a controlled manner and re-initiating the healing process. The healing response is accompanied by increased blood flow from one of the first two methods outlined. The healing with stimulus occurs with or without the long term patent or open channels and blood supply via a continuous TMR channel from the ventricle.

In one embodiment of the invention, an optical fiber having a tapered distal tip is forced through the epicardium of the ventricular wall and into the myocardium. Once into the myocardium tissue, laser energy is emitted from the distal tip of the optical fiber radially outwardly at an angle from the longitudinal axis of the fiber element.

In another embodiment, a device with multiple, narrow optical fibers is used to create a relatively dense pattern of stimulation channels. In a third modification, the epicardium may be pierced with a tapered needle for introduction therethrough of a flat ended fiber. Additionally, access through the epicardium may be made through a single hole and a laser fiber tip may be angled in different directions to create several stimulation sites.

During a typical TMR stimulus procedure according to the invention the distal tip of an optical fiber element is moved axially in increments to various depths within the myocardium. At each incremental depth, the distal tip may also be rotated as a laser pulse is emitted radially outwardly from the axis of the optical fiber. Depending on the configuration of the distal tip the laser energy may be projected in a plurality of different directions from the fiber axis. During this procedure, the laser energy is at a relatively low level that limits its travel distance within and the amount of ablation of the myocardial tissue. Each beam or burst of laser energy from the distal tip of the fiber creates a partially ablated pocket or zone wherein angiogenesis can occur due to capillary action within the pocket. Thus, for each penetration of the fiber element within the myocardium a pattern of stimulus pockets or zones are created in the tissue surrounding the fiber element. Alternatively, stimulation may be created by alternating high and low power pulses to predisposed channels that do not remain patent. In a typical TMR stimulus procedure a plurality of stimulus penetrations (e.g. 20–40) in the heart wall are made at spaced apart locations and each penetration may produce 10–20 temporary channels, pockets or zones at various depths and at different locations around the optical fiber axis. Yet, in accordance with the invention the distal tip of the optical fiber need not penetrate through the endocardium into the ventricular chamber, although such penetration is not excluded.

A device according to the invention, for controlling the penetration depth and direction of the laser energy comprises a hand-held instrument controlled by the surgeon. Within a body portion of the device a shuttle grips the fiber element to facilitate its forward and backward movement in increments. Using the device the surgeon can advance the fiber element incrementally within the myocardium as laser bursts are triggered at intervals to create stimulus zones. The full axial travel of the fiber element can be preset to limit such travel to an amount less than the thickness of the myocardium. In accordance with the invention the hand-held instrument may control the axial movement of a fiber element by mechanical or electrical means.

Other objects, advantages and features of the invention will become apparent from the following detailed description of embodiments, presented in conjunction with the accompanying drawing.

DETAILED DESCRIPTION OF DRAWING

FIGS. 2A' and 2B' are views in section showing the pattern of stimulated zones created by the device as shown in FIGS. 2A and 2B.

FIGS. 3A'–3E' are fragmentary views in elevation of the optical fiber tips shown in FIGS. 3A–3E.

FIG. 3F' is an end view of the fiber element of FIG. 3F.

FIG. 3F" is a view in elevation showing the distal end of the composite fiber element of FIG. 3F as it appears after forming stimulus zones interconnected by smaller channels within the myocardium.

DETAILED DESCRIPTION OF EMBODIMENTS

Figure 1:
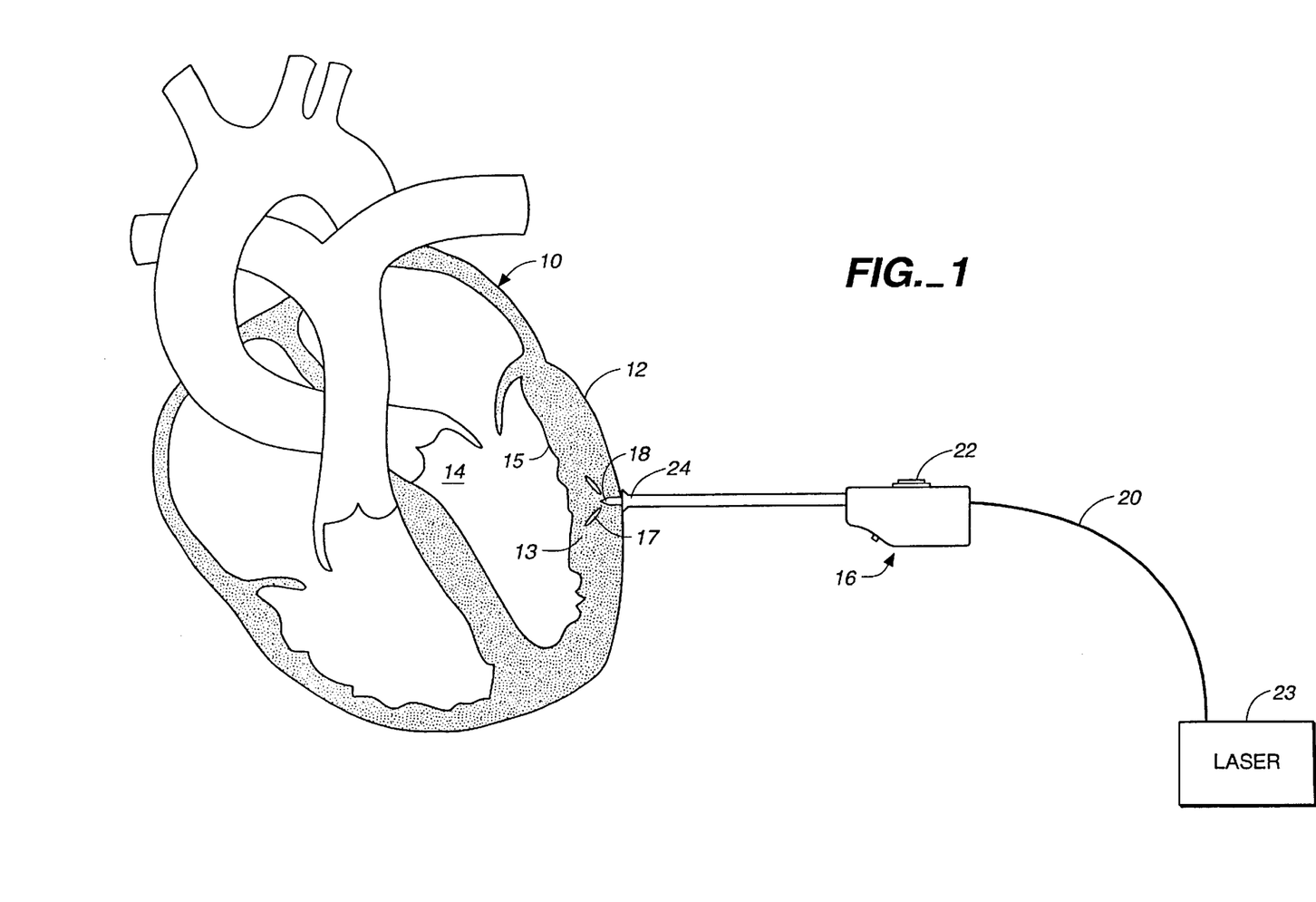
FIG. 1 is a diagrammatic view of a heart, partly in section, and showing a device for performing a stimulus type of TMR procedure according to the invention.

With reference to the drawing, FIG. 1 diagrammatically depicts a cross-section of a human heart 10 with the epicardium 12 of the outer wall of the left ventricle 14 exposed so that a stimulus type of Transmyocardial Revascularization (TMR) procedure according to the invention can be performed. Preliminary to the procedure the surgeon makes an incision or a port in the patient's chest to access or expose the outer wall (epicardium) of the heart's left ventricle. In, a human heart, the wall of the left ventricle is comprised of an outer layer or epicardium 12, the main muscle thickness or myocardium 13, and the inner layer or endocardium 15. The epicardium is comprised of a smooth, moist serous membrane which is somewhat tougher than the other tissue layers of the heart muscle.

In carrying out the method of the present invention, the surgeon may utilize a hand-held device 16 which is manipulated and operated to make a series of penetrations through the epicardium and into the myocardium of the patient's heart at selected spaced apart locations to form a multiplicity of stimulus zones 17. In this entire stimulus procedure there is no need to penetrate the endocardium layer into the ventricle cavity of the heart, although such penetration is not excluded.

In accordance with the principles of the invention, each penetration of the heart wall is made by piercing the epicardium membrane 12 with the distal end 18 of an optical fiber element 20, or by lasing through the membrane to form a relatively small opening or slit. Thereafter, the optical fiber can be moved with axial force by hand, or by any hand held device such as device 16 which can advance or reverse the fiber element by means of a movable control member 22 on the device 16 when operated by the surgeon. The optical fiber element is connected to a laser energy source 23 at its proximal end. Once through the epicardium opening and into the myocardium, laser energy is emitted from the distal tip 18 of the fiber element as it is moved forwardly incrementally through the myocardium to a preselected distance from the endocardium. As the distal end 18 of the optical fiber is moved to each incremental depth, it pauses momentarily while energy is emitted from it in a plurality of radial directions from the axis of the fiber. Each ray or segment of the laser energy emitted creates a partially ablated stimulus zone 17 to increase vascular regenesis in the myocardium tissue. After each penetration has been accomplished to form a plurality of stimulus zones, the distal end of the fiber bundle is retracted to a position within an enlarged stop member 24 at the outer end of the device 16 which can then be moved to another location to repeat the procedure. When the distal end 18 of the optical fiber element 20 is removed, the relatively small opening in the epicardium substantially closes due to the tissue resiliency, thereby minimizing any blood flow from the original penetration.

As shown in the embodiments of FIGS. 1–9, the optical fiber is a single strand preferably having a diameter of 0.5 mm to 2 mm. Other embodiments for accomplishing stimulus procedures using multi-strand optical fiber elements will be described below relative to FIGS. 11 and 13. In accordance with principles of the invention, the distal end 18 of the single optical fiber 20 may be tapered to a sharp tip to facilitate its passage through tissue of the heart by first mechanically penetrating the epicardium membrane and then moving by increments into the myocardium. Alternately, laser energy may be used to penetrate the epicardium.

Figure 3A:
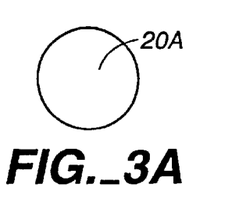
FIGS. 3A–3E are end views of various forms of optical fiber tips used with a stimulus device according to the invention.

The sharp distal tip 18 on the optical fiber 20 may be formed in different configurations, as shown in FIGS. 3A to 3E, by polishing its distal end 18 with conventional apparatus well known to those skilled in the art. For each tip configuration the direction and/or dispersion of the laser beam from the longitudinal axis of the optical fiber is different. In FIGS. 3A and 3A', an optical fiber 20A has a distal tip 18A that is beveled to form a single end face 19 which is in a plane that cuts across the optical fiber axis at a preselected angle, e.g. 45°–60°. Here, the laser beam (indicated by the dotted line) hits the end face 19 and is deflected inwardly from the fiber axis in a single beam at an angle that is 75°–90° to the end face.

Figure 3B:
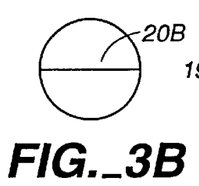

FIGS. 3B and 3B' show a single optical fiber 20B with a wedge shaped distal tip 18a formed by two facets 19a that are in planes that intersect the fiber axis at equal angles so that the wedge shaped tip subtends an angle of around 60°–75°. Here, laser energy is inwardly reflected from each of the two facets to opposite sides of the optical fiber 20a as indicated by dotted lines.

Figure 3C:
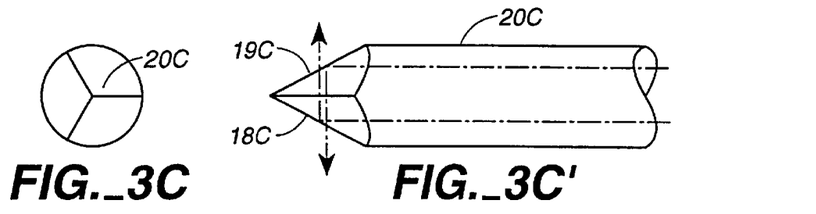
Figure 3D:
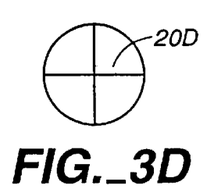

FIGS. 3C and 3C' show a distal tip 18c having three equal facets 19C, and FIGS. 3D and 3D' show a distal tip 18c having four equal facets 19D. In each case, the facets of the embodiments preferably intersect the fiber axis at the same angle (e.g. 45°–60°) and therefore have the same area and shape. The distal tip 18c with three facets cause laser energy to be directed inwardly and radially from the fiber axis in three substantially equally spaced apart directions and distal tip 18'd with four facets causes laser paths in four radial directions.

Figure 3E:
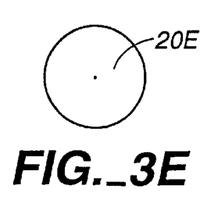

In the embodiment of FIGS. 3E and 3E', a conical distal tip 18E is provided which dispenses laser energy radially from the fiber axis in a 360° array and at a reflective angle from the angle of taper which may be from 45°–60° with respect to the fiber axis.

Figure 2A:
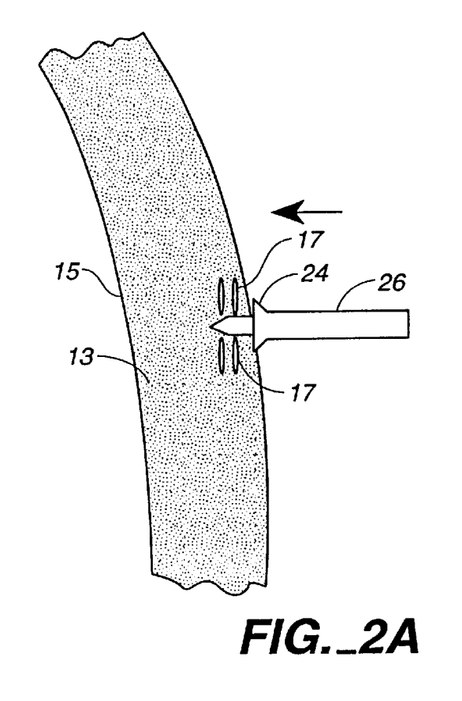
FIGS. 2A–2C are a series of enlarged views in section showing a portion of a ventricular wall of a heart as it progressively undergoes a stimulus TMR procedure according to the invention.
Figure 2B:
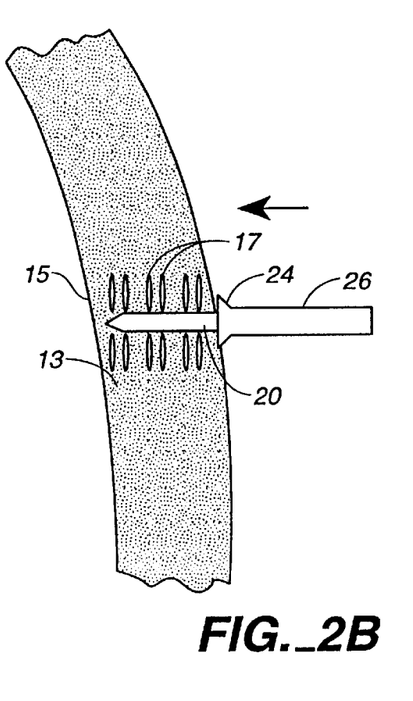
Figure 2C:
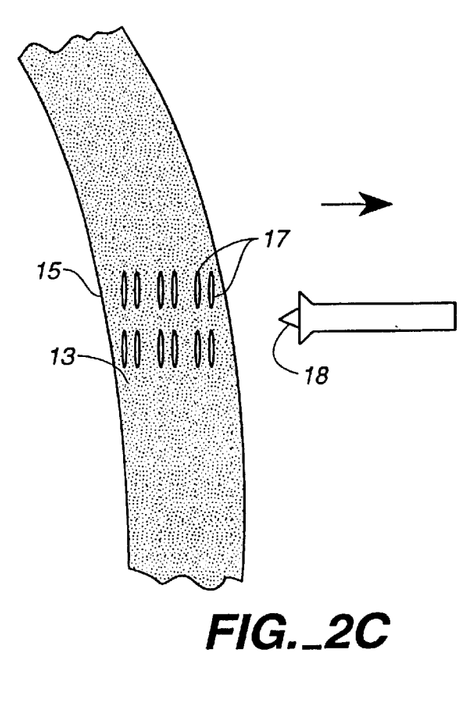

From the foregoing it is seen that depending on the selection of the distal tip for the axially movable optical fiber a preselected pattern of laser energy can be emitted from the distal tip into the myocardium tissue surrounding the optical fiber. As illustrated in FIGS. 2A–2C, the optical fiber element 20 which may have any tip configuration as shown in FIGS. 3A–3E, is moved by increments through the myocardium 13 to various depths within the tissue, but does not need to go through the endocardium 15 into the ventricular chamber. As shown in FIG. 2A, a tubular neck portion 26 through which the optical fiber element 20 is slidably retained is first positioned adjacent a target area on the outer surface of the heart. With the stop member 24 against the outer surface, the fiber element is advanced forwardly through the epicardium. After penetrating the epicardium and reaching the myocardium, a burst of laser energy is initiated to cause the distal end 18 of the optical fiber 20 to disperse the energy radially in different directions depending on the distal tip configurations. If a single facet or wedge shaped double facet configuration is used, the optical fiber can be rotated a preselected amount at the same level to increase the number of radial stimulus paths. The optical fiber element is advanced in short intervals followed by a burst of laser energy from its distal tip, as shown in FIG. 2B. Every laser beam segment which is reflected from a distal tip facet forms a limited path through the myocardial tissue, partially ablating the tissue creating a pattern of zones or pockets 17 as shown in FIGS. 2A' and 2B' wherein revascularization is stimulated by an increased capillary stimulus. The result is a regenesis of reoxygenated tissue that increases strength and vitality in the myocardium, the major heart muscle tissue.

Summarizing the action of the optical fiber element 20 during a heart muscle stimulus procedure according to the present invention, the tapered distal tip 18 is first positioned adjacent to the epicardium of the patient's heart. The optical fiber is then moved forward to penetrate through the epicardium, or laser energy is used to penetrate and enter the myocardial tissue. At this initial depth, a burst of energy is triggered and is emitted from the distal tip into the myocardial tissue at radially spaced apart locations. The fiber element may be rotated to increase the number of stimulus zones prior to another burst of laser energy. Thereafter, the fiber element is moved forwardly to another depth where another burst of laser energy is triggered. The advance, firing and rotation steps are repeated until the desired number of stimulus zones are formed in the myocardium (See FIG. 2B). When the distal tip of the optical fiber reaches a predetermined depth it is withdrawn from the heart muscle wall, as shown in FIG. 2C, and moved laterally to another location. As the distal tip is withdrawn from the epicardium, only a small opening remains which tends to close by virtue of tissue resilience so that little if any bleeding occurs.

The laser energy used in the stimulus procedures according to the present invention may be provided by a variety of laser systems. A preferred system is a Holmium:YAG laser having a wavelength range of approximately 1.8 to 2.2 um.

Figure 3F:
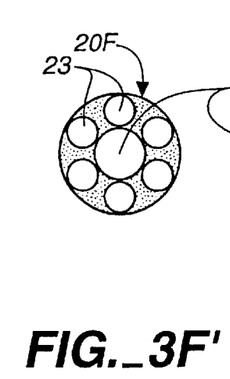
FIG. 3F is a view in elevation of the distal end of a composite fiber element.

In another form of the invention, a composite optical fiber element 20F may be used which is comprised of a bundle of fiber strands. As shown in FIGS. 3F and 3F', the composite element 20F has a larger central strand 21 having a diameter of around 0.6 mm which is surrounded by a plurality (e.g. 6) of smaller strands 23 each having a diameter of around 0.2 mm. Here, the laser system, such as a low power HO YAG laser of 0.6 J or less, operates at 10 Hz at a single wavelength but with two power level settings. The first power level with less ablating power, approximately 0.6 J, is delivered through the central strand 21 for approximately two pulses to create a narrow stimulation channel 25 having a diameter sized to form a temporary channel. The laser is preprogrammed to automatically deliver from the outer ring of fiber strands 23 a second power level with greater ablating power, approximately 1.2 to 1.65 J, or more, for approximately two pulses to create the stimulation pocket 27. Thus, as shown in FIG. 3F", a series of pockets 27 interconnected by narrow channels 25 are created during one penetration procedure. Alternately, the fiber optic element may be advanced by hand to a selected depth in the myocardium and alternating low and high power energy may be activated during retraction. It will be recognized by those skilled in the art that other lasers and laser delivery means may be used to create the pockets 27 and temporary channels 25, including laser systems having two different lasers. For example, an argon or Nd:YAG laser may be used for the outer, smaller strands 23, and a HO; YAG laser for the central strand 21. Pulses of these lasers can be programmed to alternatively deliver laser energy from the two lasers to form the stimulus pockets as shown.

Figure 8:
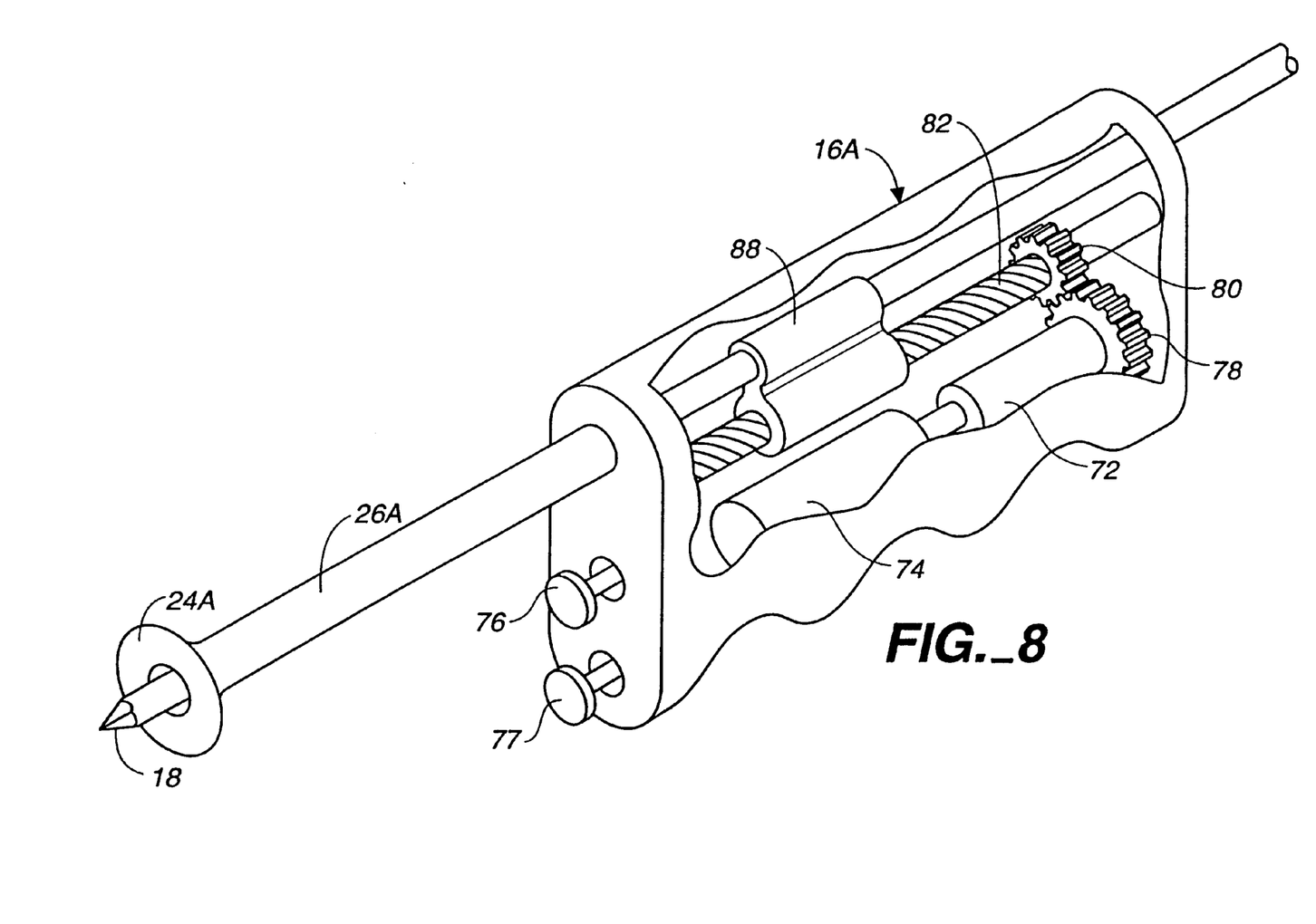
FIG. 8 is a view in perspective of an alternate form of TMR stimulus device according to the invention.
Figure 9:
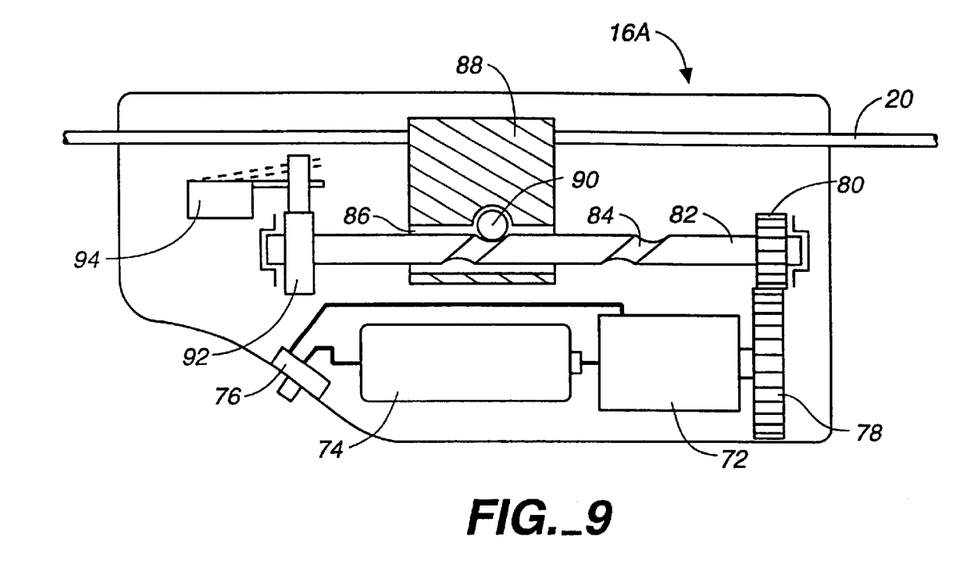
FIG. 9 is a fragmentary view in elevation and in section showing internal components of the device of FIG. 8.

The hand-held device 16 for controlling the aforesaid incremental advancement and laser firing of the optical fiber element to produce myocardium stimulation will now be described in greater detail. In the embodiment of FIGS. 4–7, the advancement device 16 is mechanically operated. A power operated device 16A is shown in FIGS. 8–9.

Figure 4:
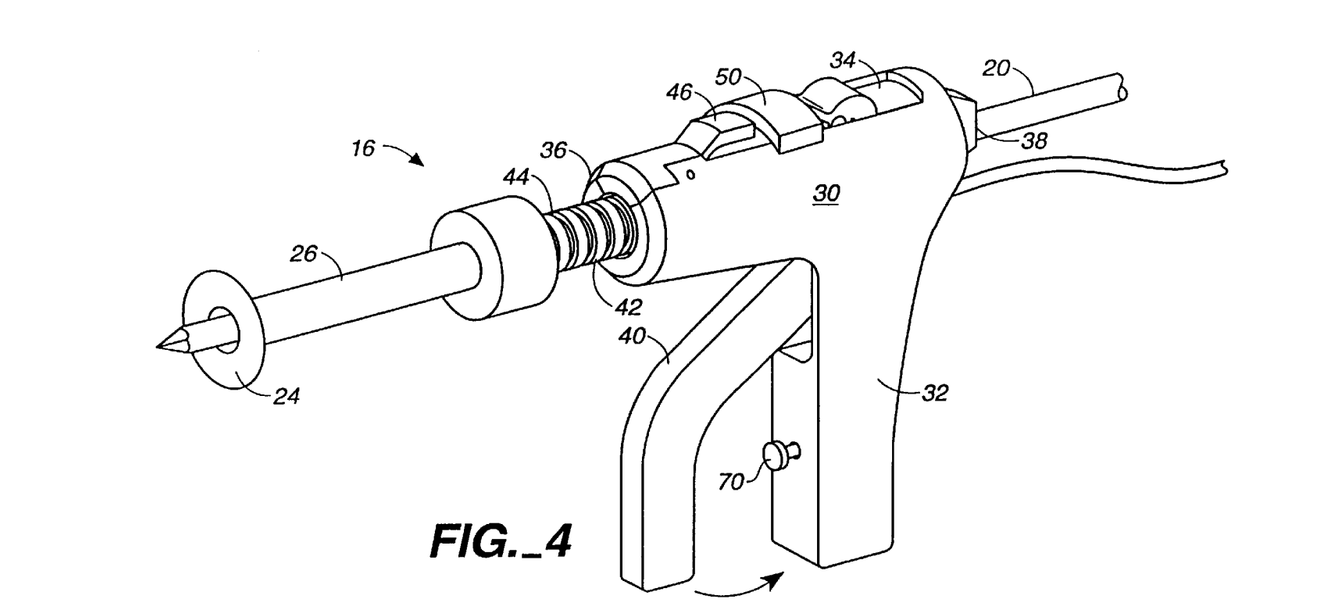
FIG. 4 is a view in perspective showing a stimulus device embodying principles of the present invention.
Figure 5:
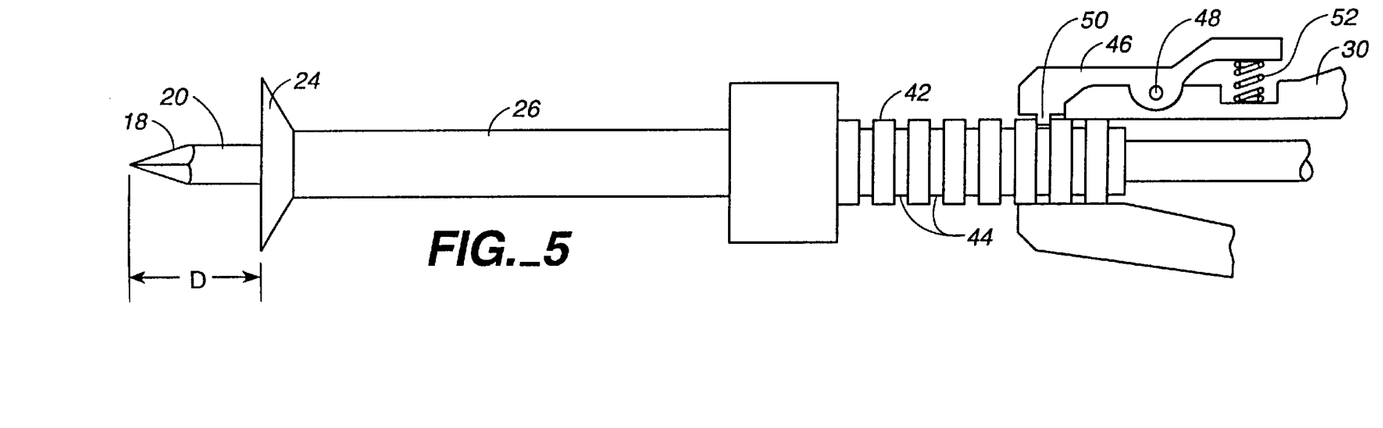
FIG. 5 is an enlarged fragmentary view in elevation showing a forward portion of the device shown in FIG. 4.

The mechanical advancement device shown in FIGS. 4–7 includes a generally pistol shaped housing 30 having a handle portion 32, a top aperture 34, front and rear apertures 36 and 38, respectively, and an operating lever 40. The neck portion 26 of the device 16 serves as a carrier tube for the axially movable optical fiber element 20. It has the stop member 24 at its outer end, and at its inner end is shaft portion 42 with a series of spaced apart circular grooves 44. As shown in FIG. 5, a tube locking member 46 is pivotally mounted by a pin 48 on the housing 30 and has a dog member 50 spaced forwardly from the pin. At the other end of the tube locking member 46 is a spring 52 which urges the dog member 50 into locking engagement with a selected groove 44 on the tube shaft 42. Release of the locking member 46 for the laser carrier tube 26 is accomplished by thumb pressure on the locking member above the spring. The laser tube 26 is movably mounted in a bore support channel (not shown) in the interior of the housing 50, so when the locking member 46 is disengaged, the tube 26 can be adjusted axially. The carrier tube's axial position controls the length of the optical laser fiber 20 that is exposed or the distance "D" of the distal tip 18 from the stop 24. This distance "D" of fiber exposure from the stop 24 corresponds to measurements of the thickness of the myocardium and the desired depth of stimulation fiber element into the myocardium. Generally, this distance "D" varies between approximately 0 to 3 cm and is set by first depressing the locking member 46 to release it and then moving the tube 26 the desired distance.

Figure 6:
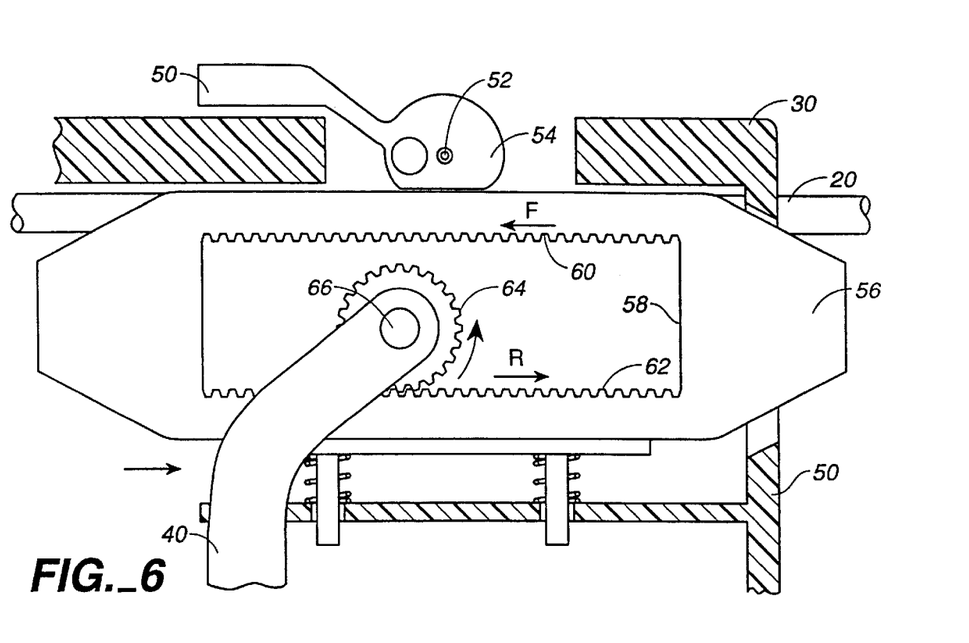
FIG. 6 is a further enlarged view in elevation and in section for the device of FIG. 4.
Figure 7:
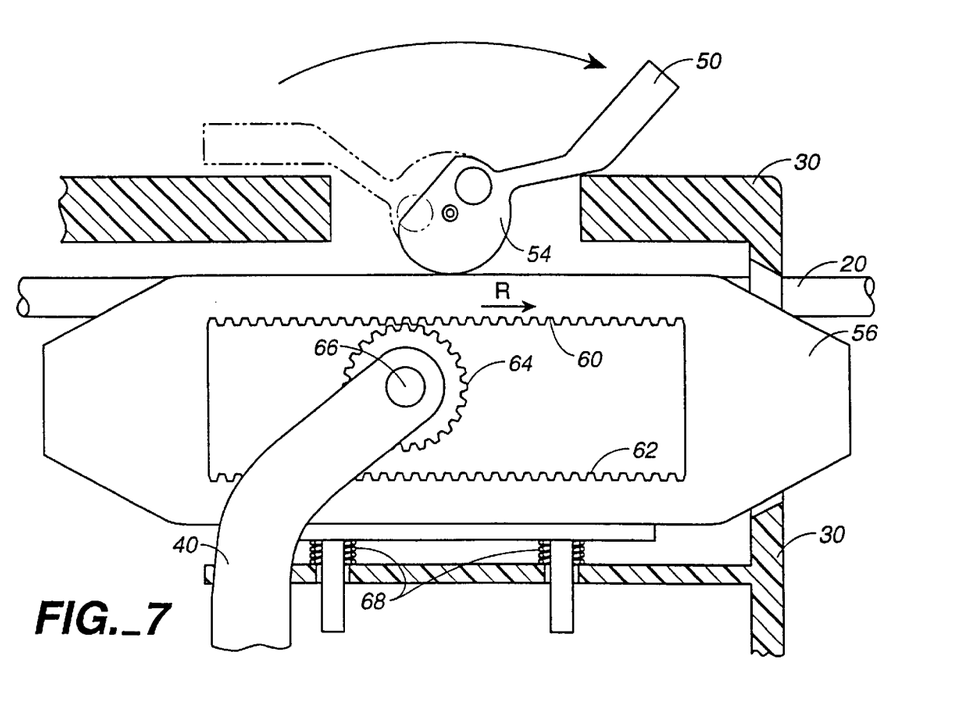
FIG. 7 is an enlarged view in elevation and in section similar to FIG. 6, but showing the device of FIG. 4 in an alternate operating mode.

Referring now to FIGS. 6–7, the means for controlling the forward and backward axial movement of the optical fiber member 20 will be described. Within the housing 30 a toggle mechanism 50 is provided which is rotatably mounted on a pin 52 and includes a camming member 54. The toggle can be moved to one of two positions to determine the direction of movement of a reciprocating rack housing 56 which is fixed to the fiber element 20 which extends through the housing 50 from the laser power source. The rack housing has an opening 58 with an upper rack 60 of gear teeth and a lower rack 62 of similar gear teeth. Operatively associated with the rack assembly is a circular gear or one way ratchet wheel 64 fixed to the pivot end of the lever 40. The lever 40 and the rachet wheel 64 are supported on an axle 66 fixed to the housing. Thus, it is seen that the fiber element 20 moves with the direction of movement of the rack housing 56.

Pressing the lever 40 in the direction of the arrow in FIG. 4 when the toggle control 50 is in the position shown in FIG. 6, causes advancement of the fiber element 20 from the distal tip by engagement of the one way rachet wheel 64 and gear rack 62 so that the rack housing moves in the forward direction "F". Movement of the toggle 50 to the reverse position shown in FIG. 7 causes the camming portion 54 to press downwardly on the rack housing 56 thereby forcing it downwardly against compression springs 68. The one way rachet wheel 64 now is engaged with the upper gear rack 60 to drive the rack in the reverse direction "R". The compression springs 68 maintain the position of the rack assembly within the housing 30. An optional laser firing button 70 may be provided on the housing handle 32 or the surgeon may control laser firing by a conventional foot switch. The advancement device components such as the housing, control level, rachet, etc. preferably may be molded from a durable plastic material such as polycarbonate or ABS.

The procedure for using the incremental laser advancement device 16 may be described as follows. First the carrier tube is set so that the distal tip of the fiber element extends the maximum distance "D" from the face of stop 24. Distance "D" is determined as the thickness of myocardium less a certain amount in order to assure that distal tip 18 will not puncture endocardium and emit laser energy into the left ventricular cavity. Now, the locking lever 46 is set on the tube by inserting its dog 50 in a groove 44 of tube. Fiber is retracted to the starting point using the rachet housing 56. The device stop 24 is placed against outer heart wall. At this point either the distal tip 18 makes an immediate penetration through the epicardium or an initial forward movement using the advancing lever 40 moves the distal tip into the myocardium. The surgeon now fires laser to create stimulus zones. The surgeon then advances the fiber 20 in small increments firing the laser at each increment using a foot switch or the like to control the laser.

As an alternative procedure, the surgeon can move the distal tip the full preset distance through the myocardium. Then, putting the rack housing 56 rachet wheel 64 in the reverse mode, using the toggle 50, the distal tip 18 is retracted in increments as the laser is fired at each increment to create the desired stimulus pattern.

As shown in FIGS. 8–9, an advancement device 16A may be electrically driven, for example, by a DC gear motor 72 which is powered by a battery 74 and controlled by a forward and reverse button switch 76 and 77. Here, the output shaft of the motor 72 is connected to a gear 78 that drives a meshed gear 80 connected to a lead screw 82 having a helical grove 84. The lead screw 82 extends through a bore 86 in a movable carriage 88 which is fixed to the fiber element 20. Within the base, the screw engages a follower 90 which is attached to the carriage. Thus, it is seen that rotation of the lead screw 82 drives the carriage and the fiber element back and forth. Fixed to one end of the lead screw is a cam 92 which engages and actuates a limit switch 94 for firing the laser at preset increments of advancement and retraction. The limit switch 94 may also be designed or wired to fire on advancement or retraction only. As shown in FIG. 8, the device 16A may also be provided with a carrier tube 26A having a flared stop member 24A at its outer end as shown on the device 16. In use, the distal tip 18 of the fiber element is positioned within the stop member during the initial contact with the epicardium of the heart during each stimulus procedure.

Figures 10, 11:
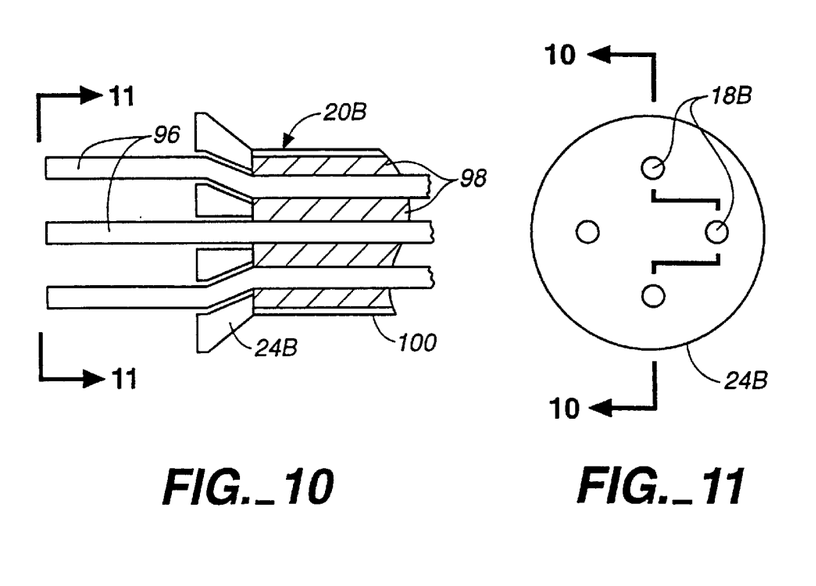
FIG. 10 is an enlarged fragmentary view in elevation of the distal end of a multi-fiber element for a stimulus device embodying principles of the invention.
FIG. 11 is an end view of the multi-fiber element of FIG. 10 taken along line 11—11 thereof.

As an alternative embodiment of the invention to the single strand or bundle version previously described, an optical fiber element may be provided which has a plurality of spaced apart strands. As shown in FIG. 10, an optical fiber element 20B has four relatively smaller optical fiber strands 96 which project outwardly like an axially parallel, spaced apart group of prongs from a transverse stop member 24B at the distal end of the fiber element 20B. Each of these smaller fiber strands 96 has a diameter of around 0.1 to 0.5 mm and their distal tips 18B may be blunt or beveled. The length of these optical prong-like strands is roughly the estimated thickness of the myocardium, e.g. 1.5 to 3.0 cm and despite their relatively small diameter these prong-like elements are quite rigid. Inwardly from the stop member 24B the smaller fiber strands 96 are preferably held together by suitable potting compound 98 which is surrounded by a plastic sheath 100.

Figures 12A, 12B:
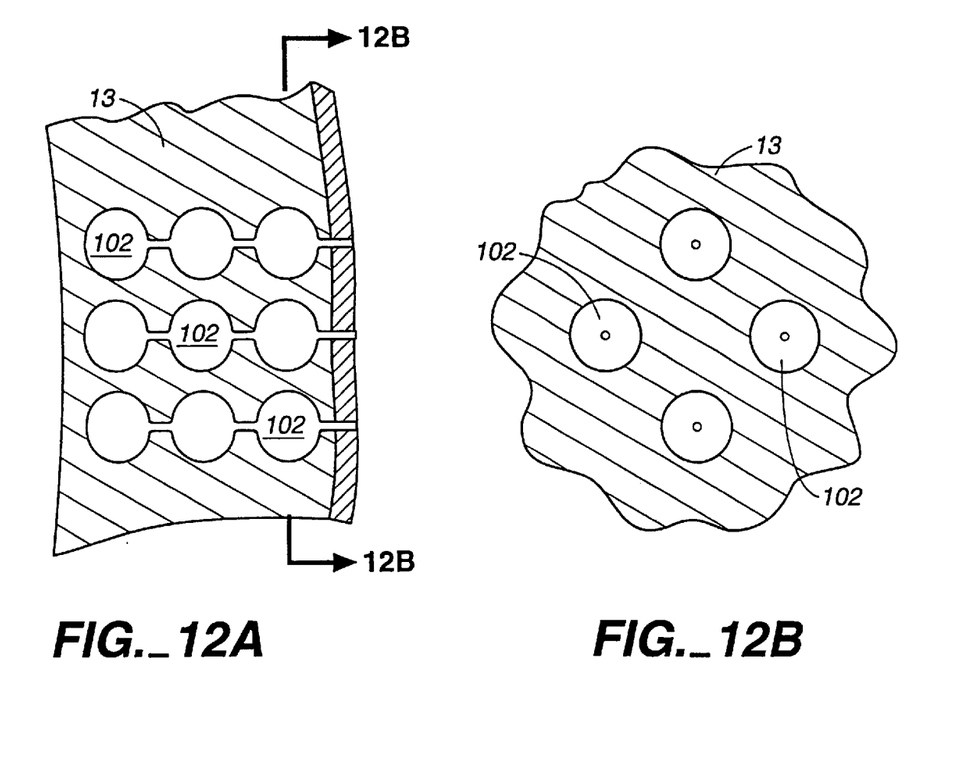
FIG. 12A is an enlarged diagrammatic view showing a section of myocardium after stimulus treatment by the multi-fiber element of FIG. 10.
FIG. 12B is a view in section taken along the line 12B—12B of FIG. 12A.

During a typical myocardial stimulus procedure using the fiber element 20B, the fiber element is pushed against the outer wall of the heart ventricle until the distal tips 18B of the spaced apart projecting strands 96 penetrate through the epicardium into the myocardium. Alternatively, laser energy may be used to penetrate the epicardium. As with previous embodiments, laser power is triggered to emit laser energy from the distal tips of the strands after they are moved forward in increments to form stimulus pockets 102 beyond each distal tip within the myocardium tissue. As laser energy is emitted from the distal end of each fiber strand 96, following each interval of penetration, a pattern of stimulus pockets 102 is created within the myocardium 13 as shown in FIGS. 12A and 12B. Alternatively, the relatively narrow fibers of this embodiment may be used to create narrow temporary channels preferably less than 0.5 mm in diameter.

Figure 13:
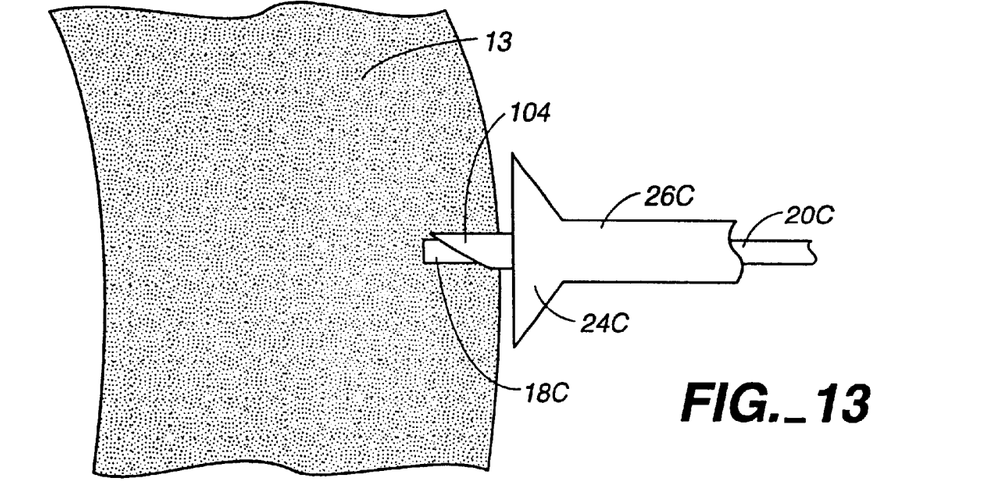
FIG. 13 is diagrammatic view in elevation of a portion of a heart wall showing a single fiber element for creating stimulus zones according to the invention.
Figure 14:
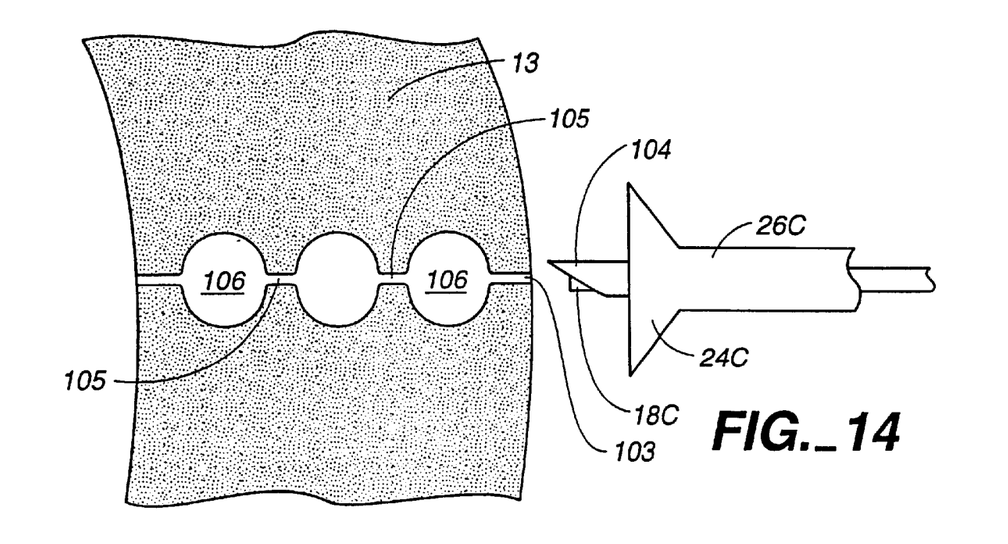
FIG. 14 is a diagrammatic view similar to FIG. 13 showing stimulus zones of various sizes just after being formed in the myocardium by using laser bursts at different power levels.

In another modified form of the invention, a single optical fiber element 20C having a diameter of around 0.5 mm is used. Here, as shown in FIGS. 13 and 14, the smaller fiber element which has a blunt or beveled distal tip 18C is placed against the ventricle wall of the heart. Here, the fiber element 20C preferably extends through a tubular carrier tube 26C having a flared stop member 24C at its distal end which is provided with a hollow piercing member 104. The piercing member forms a small opening 103 in the epicardium membrane before the fiber element is advanced through the piercing member into the myocardium 13. Once into the myocardium tissue, laser energy of relatively low power, 0.6 J, is transmitted through the distal tip to create a small connecting, temporary channel 105. Thereafter, a burst of laser energy of increased power (e.g. 1.2–1.65 J) is triggered from the distal tip of the fiber element to form a larger stimulus pocket 106 (FIG. 14). As the distal tip of the fiber element moves forward and pauses, it emits alternating bursts of low power and high power laser energy thereby forming a series of spaced apart stimulus pockets 106 of partially ablated tissue connected by narrow channels in the myocardium. After the distal tip has moved to a position near the endocardium, the fiber element 20C is retracted and then moved laterally to an adjacent position to repeat the process.

Figure 15:
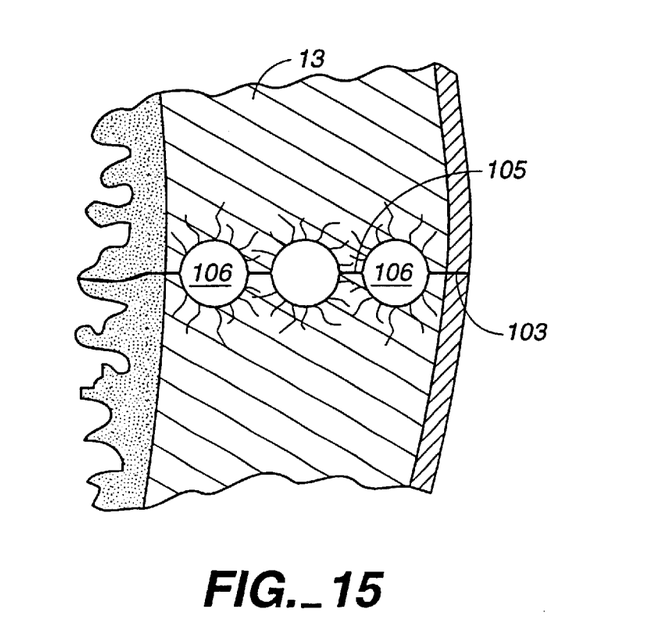
FIG. 15 is a diagrammatic view similar to FIG. 14 showing how the stimulus zones in the myocardium indicate a regenesis of capillary tissue after an elapse of time from the stimulus procedure.

After a period of time following the procedure illustrated in FIG. 14, the myocardium tissue naturally regenerates as shown in FIG. 15. The opening 103 in the epicardium heals over and closes as do the narrow channels 105, leaving the spaced apart zones 106 wherein regenesis of the capillary system occurs to revitalize the heart muscle.

To those skilled in the art to which this invention relates, many changes in construction and widely differing embodiments and applications of the invention will make themselves known without departing from the spirit and scope of the invention. The disclosure and the description herein are purely illustrative and are not intended to be in any sense limiting.

What is claimed is:

1. An apparatus for stimulating angiogenesis in myocardium, the apparatus comprising:

a body member;

a neck member connected to said body member;

a neck adjustment mechanism for adjusting said neck member relative to said body member having a distal section slidably connected within said body member, wherein a proximal section of said neck adjustment mechanism has a series of grooves;

a head member connected to a proximal end of said neck member, said head member defining a stop member adapted for engaging a heart;

a laser energy delivery device for ablating tissue to form stimulating zones having a distal end and a proximal end configured to optically connect to a laser energy source, and translatable through and egressible from said head member;

a laser energy delivery device advancement mechanism attached to said body member for controlling by discrete and incremental movement said distal end of said laser energy delivery device to pre-selected positions relative to said head member, whereby firing said laser energy delivery device reproducibly creates said stimulating zones at said pre-selected positions; and a locking member pivotally attached to said body member having a distal end with a projection configured to fit within one of said series of grooves and a proximal end having a thumb actuated portion connected to a spring bias member for urging engagement of said projection into one of said series of grooves, whereby when said locking member is disengaged said neck member can be adjusted thereby adjusting a length of exposure of said distal end of said laser energy delivery device from said stop member.

2. The apparatus of claim 1 wherein said laser energy delivery device comprises an optical fiber element having a tapered distal end and at least one outer surface lying in a plane forming an oblique angle with respect to a longitudinal axis of said optical fiber element, whereby laser energy transmissions from said distal end of said optical fiber element form at least one outwardly directed a beam from said longitudinal axis of said optical fiber element.

3. The apparatus of claim 1 wherein said laser energy delivery device comprises an optical fiber element having a tapered distal end with a plurality of outer surfaces, each of said plurality of outer surfaces being in a plane forming an oblique angle with respect to a longitudinal axis of said optical fiber element, whereby laser energy transmissions from said distal end of said optical fiber element form outwardly directed beams from said longitudinal axis of said optical fiber element.

4. The apparatus of claim 1 further including a how piercing element for tissue penetration connected to said head member, said distal end of said laser energy delivery device translatable through said hollow piercing element.

5. The apparatus of claim 1 wherein said laser energy delivery device further includes an adaptive control mechanism for operating said laser source at variable power levels.

6. The apparatus of claim 1 wherein said laser energy delivery device advancement mechanism includes a shuttle having first and second spaced apart internal gear racks, a driving gear between said gear racks and connected to an operating handle, and further comprising a directional control mechanism fixed to said laser energy delivery device for controlling directional movement of said laser energy delivery a device.

7. The apparatus of claim 6 wherein said directional control mechanism includes:
   at least one spring extending between an interior portion of said body member and said shuttle such that when said driving gear is urged into engagement with said first gear rack, said laser energy delivery device is advanced and when said driving gear is urged into engagement with said second gear rack, said a laser energy delivery device is retracted; and
   a pivotal member having a cam portion adapted to bear against and move said shuttle against said at least one spring so that said driving gear engages said second gear rack.

8. The apparatus of claim 1 wherein said laser energy delivery device comprises a plurality of spaced apart parallel optical fiber strands having distal tips.

9. The apparatus of claim 8 wherein said distal tips of said optical fiber strands have a diameter of about 0.1 to 0.5 mm and can extend about 1.5 to 3.0 cm beyond said head member.

10. The apparatus of claim 1 wherein said laser energy delivery device comprises a central optical fiber strand surrounded by a plurality of outer optical fiber strands having a smaller diameter than said central optical fiber.

11. The apparatus of claim 10 wherein said central optical fiber strand has a diameter of around 0.6 mm and said outer fiber optical strands have a diameter of around 0.2 mm.

12. The apparatus of claim 10 wherein said central optical fiber has a proximal end configured to connect to an argon or Nd:YAG laser and said outer optical fiber strands have proximal ends configured to connect to a holmium (Ho:YAG) laser.

13. The apparatus of claim 10 wherein said central and outer optical fiber strands have flat, non-tapered end faces it are perpendicular to a longitudinal axis of said central and outer optical fiber strands.

* * * * *

UNITED STATES PATENT AND TRADEMARK OFFICE
CERTIFICATE OF CORRECTION

PATENT NO. : 6,620,153 B2
DATED : September 16, 2003
INVENTOR(S) : Mueller et al.

It is certified that error appears in the above-identified patent and that said Letters Patent is hereby corrected as shown below:

<u>Column 10,</u>
Line 42, delete "a".
Line 53, "how" should read -- hollow --.

<u>Column 11,</u>
Line 8, delete "a".

Signed and Sealed this

Sixteenth Day of December, 2003

JAMES E. ROGAN
*Director of the United States Patent and Trademark Office*